United States Patent
Johnsen et al.

(10) Patent No.: US 9,372,158 B2
(45) Date of Patent: Jun. 21, 2016

(54) PROJECTION LASER PROFILER

(71) Applicant: Jennison Corporation, Carnegie, PA (US)

(72) Inventors: Mark P. Johnsen, Pittsburgh, PA (US); Theodore J. Cooper, Pittsburgh, PA (US)

(73) Assignee: Jennison Corporation, Carnegie, PA (US)

( * ) Notice: Subject to any disclaimer, the term of this patent is extended or adjusted under 35 U.S.C. 154(b) by 48 days.

(21) Appl. No.: 13/799,938

(22) Filed: Mar. 13, 2013

(65) Prior Publication Data

US 2014/0055793 A1    Feb. 27, 2014

Related U.S. Application Data

(60) Provisional application No. 61/692,877, filed on Aug. 24, 2012.

(51) Int. Cl.
| | |
|---|---|
| *G01B 11/24* | (2006.01) |
| *G01N 21/88* | (2006.01) |
| *G01N 21/954* | (2006.01) |
| *E03F 7/12* | (2006.01) |
| *G01C 15/00* | (2006.01) |

(52) U.S. Cl.
CPC .............. *G01N 21/8806* (2013.01); *E03F 7/12* (2013.01); *G01C 15/004* (2013.01); *G01N 21/954* (2013.01)

(58) Field of Classification Search
CPC ..... G01N 21/954; G01N 21/86; G01N 21/88; G01N 21/00; G01B 11/24; G01B 11/12
USPC .................. 356/601–614, 241.1; 250/559.19, 250/559.22, 559.24
See application file for complete search history.

(56) References Cited

U.S. PATENT DOCUMENTS

| | | |
|---|---|---|
| 4,967,092 A | 10/1990 | Fraignier et al. |
| 5,895,927 A | 4/1999 | Brown |
| 6,043,879 A | 3/2000 | Dong |
| 6,546,636 B2 | 4/2003 | Tamamura |
| 7,046,356 B2 | 5/2006 | Bondurant |
| 7,164,476 B2 | 1/2007 | Shima et al. |
| 8,035,823 B2 | 10/2011 | Keightley et al. |
| 8,045,145 B1* | 10/2011 | Bakker et al. .............. 356/237.2 |
| 2003/0198374 A1* | 10/2003 | Hagene et al. ................ 382/141 |
| 2004/0020270 A1* | 2/2004 | Kuikka .......................... 73/49.5 |
| 2004/0021858 A1* | 2/2004 | Shima ................... G01N 21/954 356/241.1 |
| 2004/0114793 A1* | 6/2004 | Bondurant ........... G01N 21/954 382/141 |
| 2005/0237519 A1* | 10/2005 | Bondurant et al. ......... 356/241.1 |
| 2007/0139658 A1* | 6/2007 | Riul et al. ..................... 356/612 |
| 2008/0105067 A1* | 5/2008 | Frey ....................... G01B 11/24 73/865.8 |
| 2010/0094138 A1 | 4/2010 | Gharib et al. |
| 2011/0235057 A1 | 9/2011 | Storksen et al. |

FOREIGN PATENT DOCUMENTS

CA           2216800 A1    10/1996

* cited by examiner

*Primary Examiner* — Tarifur Chowdhury
*Assistant Examiner* — Isiaka Akanbi
(74) *Attorney, Agent, or Firm* — The Webb Law Firm (57) ABSTRACT

A laser profiler includes: a laser diode mounted within a substantially cylindrical housing; a conical mirror positioned upstream from the laser diode within the cylindrical housing; and a transparent shroud positioned to surround the conical mirror. A beam produced by the laser diode is directed to the conical mirror and is reflected therefrom at 360° through the transparent shroud to produce a ring of light.

7 Claims, 8 Drawing Sheets

PROJECTION LASER PROFILER

CROSS REFERENCE TO RELATED APPLICATIONS

This application claims the benefit of U.S. Provisional Patent Application No. 61/692,877 entitled "Projection Laser Profiler" filed Aug. 24, 2012, which is hereby incorporated by reference in its entirety.

BACKGROUND OF THE INVENTION

1. Field of the Invention

The present invention, in general, is directed to a system and method for profiling the interior of a pipeline and, more specifically, for a system and method for profiling the interior of a pipeline by projecting a 360° ring of laser light onto the interior of the pipeline.

2. Description of Related Art

Known systems for profiling or inspecting pipelines typically comprise a television camera or a video camera mounted on a self-propelled electric tractor or on a sled pushed by a semi-rigid cable along the pipe from an open end of the pipe. Lights are attached to illuminate the pipeline interior. Both the lights and the camera are powered by the cable. An image of the pipeline is captured by the camera and recorded by a recording device for viewing.

Currently, laser profilers are used in conjunction with such systems to collect survey data and create pipeline reports containing the measurement of faults and other features inside a pipeline. This is done by projecting a 360° ring of laser light onto the internal pipe surface. The laser image is viewed via the camera and analyzed by software to build a digital pipe profile.

Typical laser profilers are designed to employ a circular array of line emitting lasers to project the light ring. However, a line laser projected onto the interior surface will have a varying line thickness. Also, the adjacent lasers project lines that overlap causing additional line thickness variations. These line thickness inconsistencies result in inaccurate data surveys and unreliable information. Furthermore, the alignment of the rotational aspect of adjacent lasers is a time consuming task in order to yield a clean ring of light.

Accordingly, a need exists for a laser profiler that eliminates the need for a plurality of redundant laser diodes. A further need exists for a laser profiler that eliminates alignment issues and produces a crisp ring of light having a uniform width.

SUMMARY OF THE INVENTION

An object of the present invention is to provide a laser profiler that utilizes a single diode, thereby eliminating the need for a plurality of redundant laser diodes. An additional object of the present invention is to eliminate alignment issues with the laser diodes by providing a single laser diode. In addition, it is an object of the present invention to provide a laser profiler that produces a crisp ring of light having a uniform width such that accurate data surveys and reliable information can be obtained.

Accordingly, provided is a laser profiler that includes: a laser diode mounted within a substantially cylindrical housing; a conical mirror positioned upstream from the laser diode within the cylindrical housing; and a transparent shroud positioned to surround the conical mirror. A beam produced by the laser diode is directed to the conical mirror and is reflected therefrom at 360° through the transparent shroud to produce a ring of light.

In one embodiment, the cylindrical housing may include a base, a first flange portion connected to the base, and a second flange portion and a mirror mount portion forming the top of the cylindrical housing. The transparent shroud may be secured between the first flange portion and the second flange portion to establish a connection between the first flange portion and the second flange portion and the mirror mount portion. The first flange portion and the mirror mount portion of the cylindrical housing may be machined to a shape to shield misaligned light reflected from the conical mirror from passing through the transparent shroud to ensure that the ring of light has a uniform width. The laser diode may be positioned at least partially within the first flange portion. The base of the cylindrical housing may include a connection port for supplying power to the laser diode.

Alternatively, the cylindrical housing may include a base, a shroud assembly having the transparent shroud positioned therein, and an end cap. The shroud assembly may include an upper threaded portion threadedly coupled to the end cap, a lower threaded portion threadedly connected to the base, an upper shielding portion extending from the upper threaded portion over a portion of the transparent shroud, and a lower shielding portion extending from the lower threaded portion over a portion of the transparent shroud. The upper shielding portion and the lower shielding portion of the shroud assembly may be machined to a shape to shield misaligned light reflected from the conical mirror from passing through the transparent shroud to ensure that the ring of light has a uniform width.

Also provided is an apparatus for profiling an interior of a pipeline that includes: a vehicle configured to be moved through the pipeline; a laser profiler mounted on the vehicle and configured to project a 360° ring of laser light onto the interior of the pipeline; and a camera mounted on the vehicle configured to obtain an image of the 360° ring of light. The laser profiler includes: a laser diode mounted within a substantially cylindrical housing; a conical mirror positioned upstream from the laser diode within the cylindrical housing; and a transparent shroud positioned to surround the conical mirror. A beam produced by the laser diode is directed to the conical mirror and is reflected therefrom at 360° through the transparent shroud to produce the 360° ring of light. The vehicle may be either a self-propelled electric tractor or a sled pushed or pulled by a cable through the pipeline.

In addition, provided is a method for profiling an interior of a pipeline. The method includes providing a laser profiler. The laser profiler includes a laser diode mounted within a substantially cylindrical housing; a conical mirror positioned upstream from the laser diode within the cylindrical housing; and a transparent shroud positioned to surround the conical mirror. A beam produced by the laser diode is directed to the conical mirror and is reflected therefrom at 360° through the transparent shroud to produce a 360° ring of light. The method also includes: projecting the 360° ring of light onto the interior of the pipeline; moving the laser profiler through the pipeline; imaging the 360° ring of light with a camera as it moves through the pipeline; and analyzing the images with software to produce a digital pipe profile.

These and other features and characteristics of the present invention, as well as the methods of operation and functions of the related elements of structures, will become more apparent upon consideration of the following description and the appended claims with reference to the accompanying drawings, all of which form a part of this specification, wherein like reference numerals designate corresponding parts in the various figures. As used in the specification and the claims, the singular form of "a", "an", and "the" include plural referents unless the context clearly dictates otherwise.

DESCRIPTION OF THE INVENTION

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification are simply exemplary embodiments of the invention. Hence, specific dimensions and other physical characteristics related to the embodiments disclosed herein are not to be considered as limiting.

With reference to FIGS. 1-4, a laser profiler, generally denoted as reference numeral 2, includes a generally cylindrical housing, generally denoted as reference numeral 4, having a base 6, a first flange portion 8 connected to the base 6, and a second flange portion 10 and a mirror mount portion 12 forming the top of the cylindrical housing 4. The second flange portion 10 is connected to the mirror mount portion 12 through the use of any suitable fastening device, such as bolts 14. A sealing device, such as o-ring 16, may be provided between the second flange portion 10 and the mirror mount portion 12 to ensure that the cylindrical housing 4 is fluid tight. The first flange portion 8 is connected to the base 6 through the use of any suitable fastening device, such as bolts 18. A sealing device, such as o-ring 20, may be provided between the first flange portion 8 and the base 6 to ensure that the cylindrical housing 4 is fluid tight. A transparent shroud 22 is secured between the first flange portion 8 and the second flange portion 10 to establish a connection between the first flange portion 8 and the second flange portion 10 and the mirror mount portion 12.

The transparent shroud 22 may be manufactured from any suitable material such as clear cast acrylic. However, desirably the transparent shroud 22 is manufactured from borosilicate glass. The improvement in clarity of borosilicate glass over a transparent plastic material resulted in a significantly improved uniformity of power readings along the projected laser ring. In addition, power loss of the laser occurs as the laser light passes through the borosilicate shroud. For instance, if a 30 milliwatt laser source is utilized, by passing the laser light through the borosilicate glass shroud, the laser light is reduced to 1 milliwatt at 70 millimeters from the outside diameter of the shroud. Accordingly, since the laser profiler can be operated to produce laser light that is less than 1 milliwatt, it qualifies as a class II laser, which does not require the use of protective eye glasses by a user. The desired power loss was developed by adjusting the sidewall thickness of the borosilicate glass transparent shroud.

Figure 1:
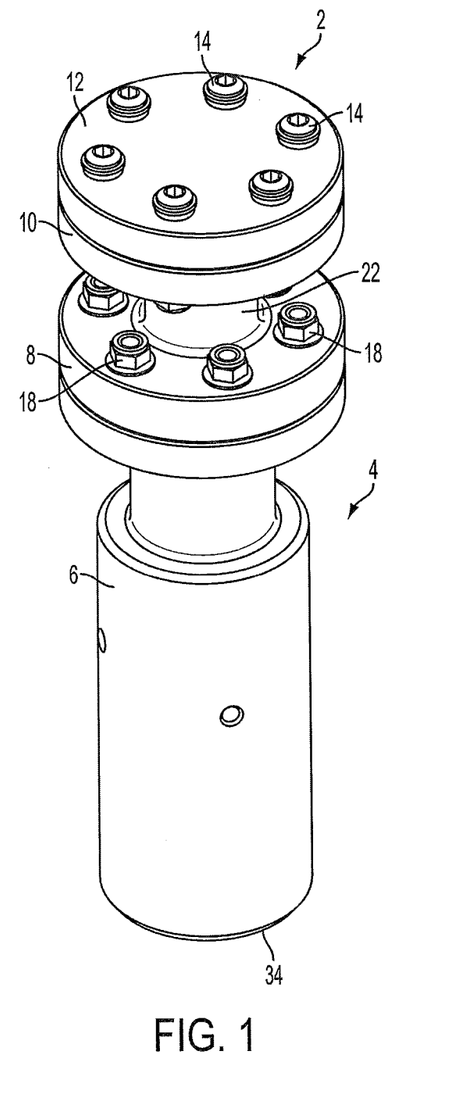
FIG. 1 is a perspective view of a laser profiler in accordance with the present invention.
Figure 2:
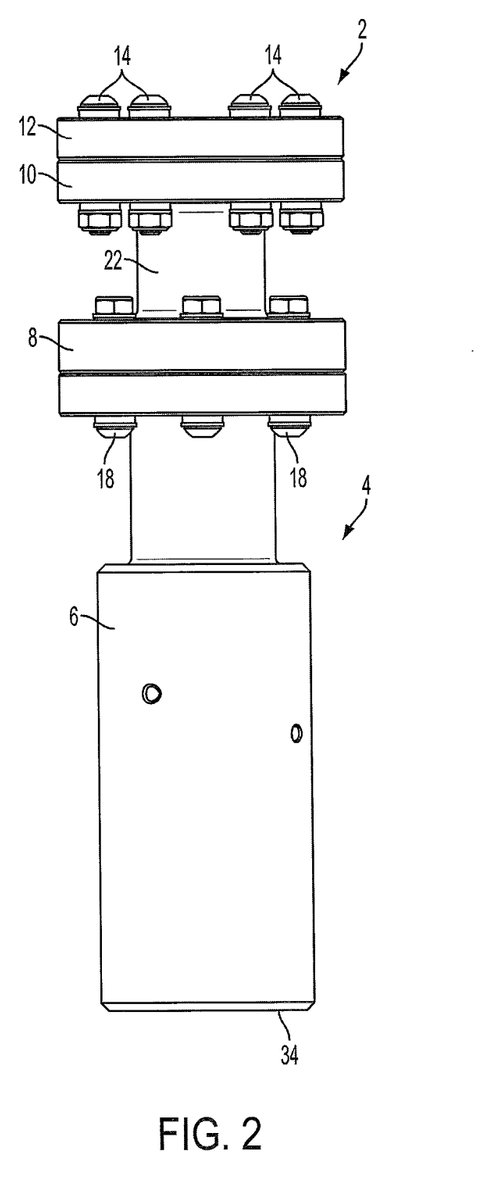
FIG. 2 is a front plan view of the laser profiler of FIG. 1.
Figure 3:
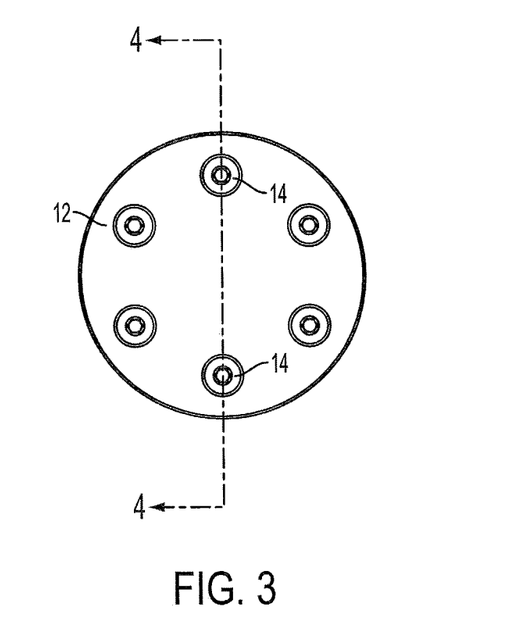
FIG. 3 is a top view of the laser profiler of FIG. 1.
Figure 4:
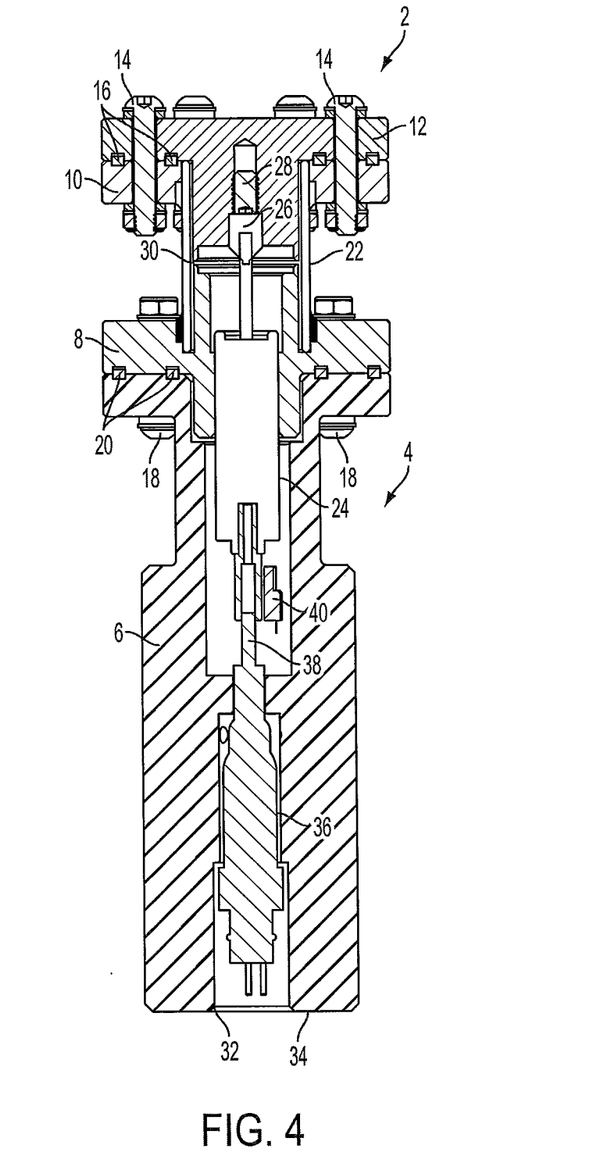
FIG. 4 is a cross-sectional view of the laser profiler of FIG. 3 taken along line 4-4.

With specific reference to FIG. 4 and continuing reference to FIGS. 1-3, a single laser diode 24 is mounted within the substantially cylindrical housing 4 to the first flange portion 8. The laser diode 24 may be a single elliptical beam laser diode, such as an industrial 30 MW laser manufactured by ProPhotonix, a circular beam laser diode, or any other suitable laser diode. A conical mirror 26 is positioned upstream from the laser diode 24 within the cylindrical housing 4. The conical mirror 26 is mounted to the mirror mount portion 12 by a screw 28 or other suitable fastening device. The transparent shroud 22 is positioned to surround the conical mirror 26. The first flange portion 8 and the mirror mount portion 12 of the cylindrical housing 4 are machined to a shape to form a gap 30 to allow laser light to leave the cylindrical housing 4. Accordingly, the first flange portion 8 and the mirror mount portion 12 shield misaligned light reflected from the conical mirror 26 from passing through the transparent shroud 22 to ensure that a ring of light produced by the profiler 2 has a uniform width.

The base 6 of the cylindrical housing 4 includes a connection port 32 on a bottom surface 34 thereof for supplying power to the laser diode 24. An electric connection component 36, DC jack 38, and line regulator and general purpose voltage blocking diode 40 are positioned within the connection port 32 to supply power to the laser diode 24.

The base 6, the second flange portion 10, and the mirror mount portion 12 may be manufactured from plastic. However, this is not to be construed as limiting the present invention as any suitable, durable material may be utilized. For instance, each of these components may be manufactured from anodized aluminum. In addition, the first flange portion 8 may be manufactured from aluminum to act as a heat sink for the laser diode 24. This is also not to be construed as limiting the present invention as any suitable material with heat sink capabilities may be utilized.

In operation, the laser diode 24 produces a beam of light that is directed to the conical mirror 26. The conical mirror 26 receives the beam of light and reflects the beam therefrom at 360° through the transparent shroud 22 to produce a ring of light on the surface surrounding the laser profiler 2, such as a pipeline.

Figure 5:
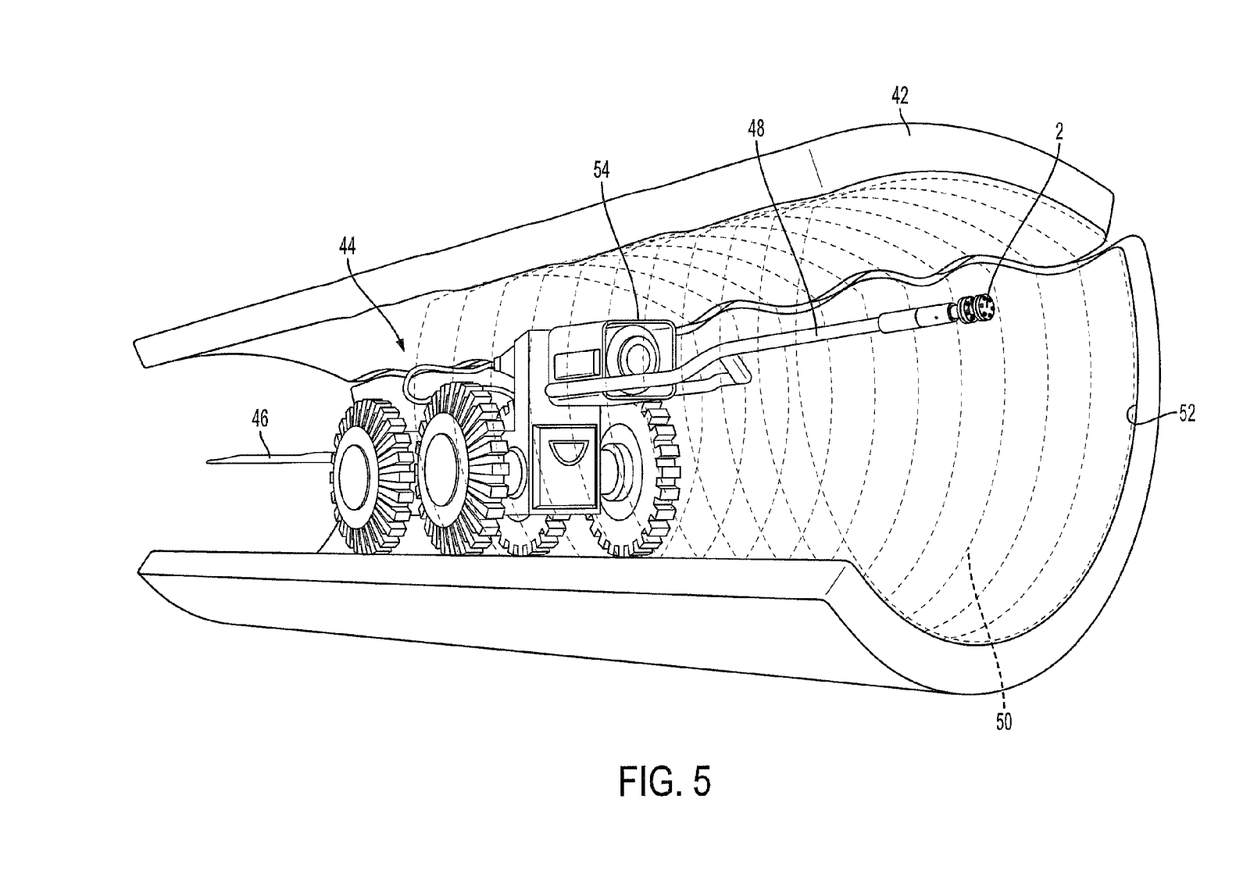
FIG. 5 is a perspective view of the laser profiler of FIG. 1 mounted to an electric tractor moving through a pipeline.

With reference to FIG. 5, the laser profiler 2 described hereinabove may be provided as part of an apparatus for profiling an interior of a pipeline 42. Such an apparatus generally includes a vehicle, generally denoted as reference numeral 44, configured to be moved through the pipeline 42. As illustrated in FIG. 5, the vehicle 44 may be a self-propelled electric tractor. Such a tractor may include a cable 46 provided to transmit information obtained by the apparatus to a remote location. Alternatively, the vehicle 44 may be sled pushed or pulled through the pipeline 42 by a cable. The laser profiler 2 is mounted on the vehicle 44 on a pole 48 positioned forwardly of a front end of the vehicle 44. As described hereinabove, the laser profiler 2 is configured to project a 360° ring of laser light 50 onto an interior surface 52 of the pipeline 42. The apparatus also includes a camera 54 mounted on the vehicle 44 and configured to obtain an image of the 360° ring of light 50.

In operation, the vehicle 44 is positioned within the pipeline 42 and travels through pipeline 42. As the vehicle 44 moves through the pipeline 42, the laser profiler 2 projects the 360° ring of light 50 onto the interior surface 52 of the pipeline 42. The 360° ring of light 50 is imaged with the camera as the vehicle 44 and the ring of light 50 moves through the pipeline 42. Finally, software is utilized to analyze the images to produce a digital pipe profile.

With reference to FIGS. 6-9, an alternative embodiment of the laser profiler is illustrated. This laser profiler functions the same as the laser profiler 2 of FIGS. 1-4 in that it includes a laser diode that directs a beam of light onto a conical mirror which then reflects the beam of light at 360° through a transparent shroud to produce a ring of light on the surface surrounding the laser profiler. However, the cylindrical housing of this laser profiler is configured differently such that the use of bolts 14 to attach the mirror mount portion 12 and the second flange 10 together and the use of bolts 18 to connect the first flange portion 8 to the base 6 are eliminated. This allows the overall size of the laser profiler to be manufactured at a reduced size and reduced weight. The size reduction increases the range of pipe diameters it can be used in. This eliminates the need for multiple sizes of laser profiler units to satisfy a range of pipe diameters. Weight reduction increases the rigidity of the unit at its mounting location. This results in less "bouncing around" of the laser profiler during linear movement so the projected ring is more stable.

Figure 6:
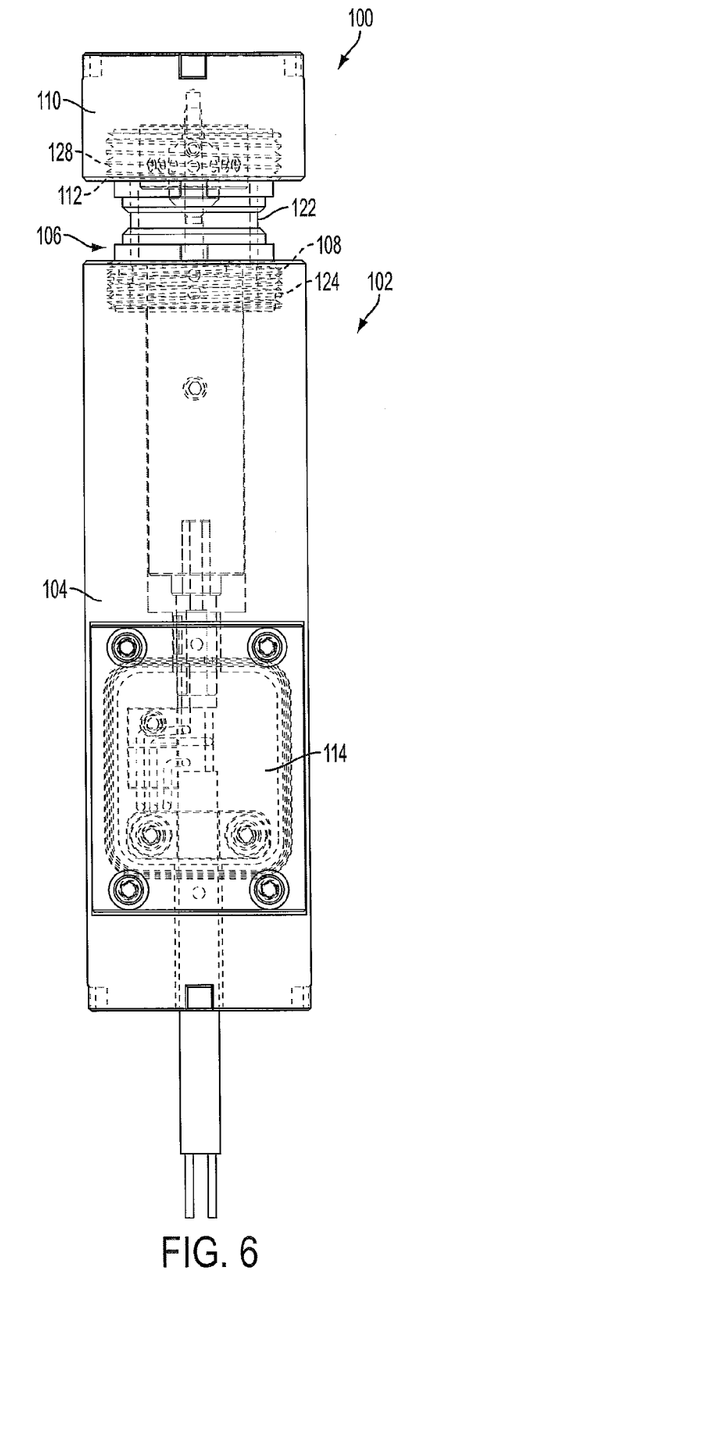
FIG. 6 is a front plan view of a laser profiler in accordance with an alternative embodiment of the present invention.
Figure 7:
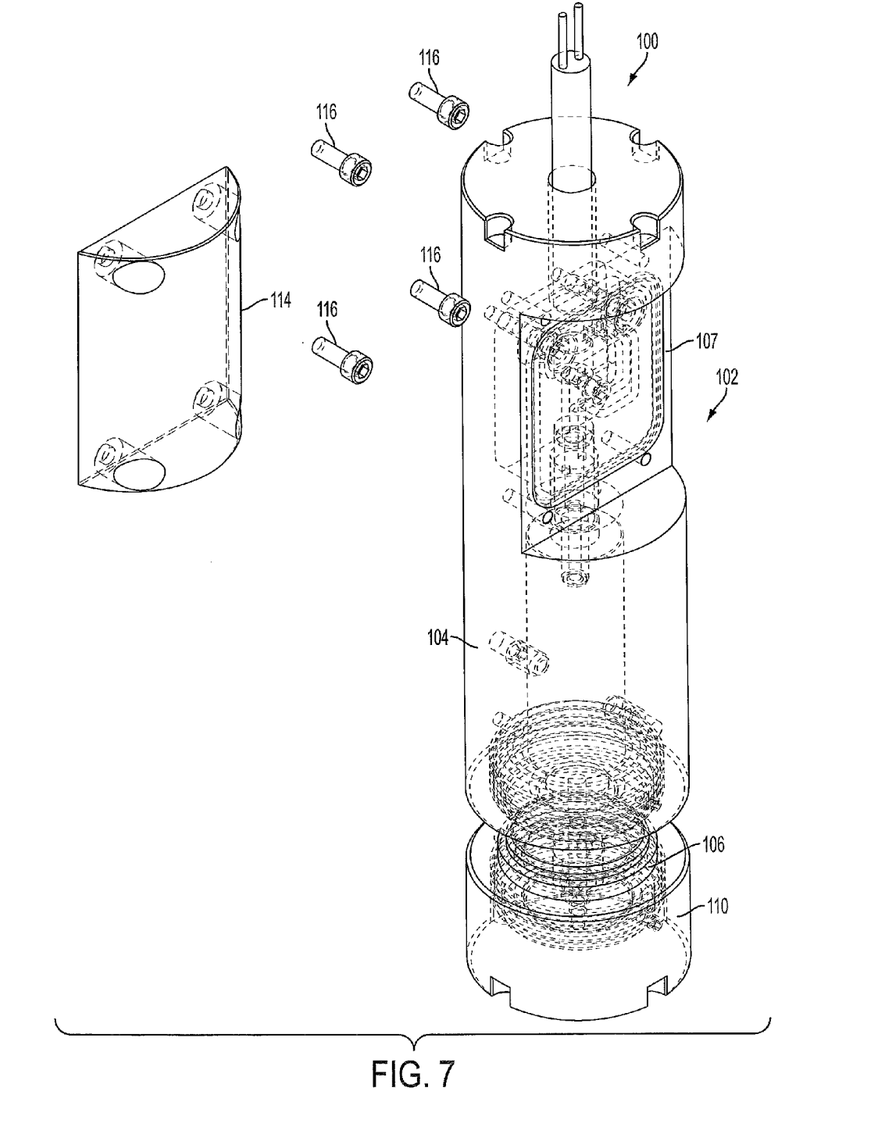
FIG. 7 is a partially exploded, perspective view of the laser profiler of FIG. 6.

More particularly, the laser profiler of the alternative embodiment, generally denoted as reference numeral 100, includes a generally cylindrical housing, generally denoted as reference numeral 102, having a base 104, a shroud assembly 106 having a first end 108 threadedly connected to the base 104, and an end cap 110 threadedly connected to a second end 112 of the shroud assembly 106 forming the top of the cylindrical housing 102. The base 104 may include an access door 114 that is secured to the base 104 through the use of any suitable fastening device, such as bolts 116. A sealing device, such as o-ring 107, may be provided between the base 104 and access door 114 to ensure that the cylindrical housing 102 is fluid tight. The access door 114 allows a user to have easy access to the electrical components of the laser profiler 100 for maintenance purposes. The laser diode is positioned within the base 104 and may extend partially into the shroud assembly 106. Accordingly, the base and the shroud assembly may be manufactured from a material such as aluminum to act as a heat sink for the laser diode.

Figure 8:
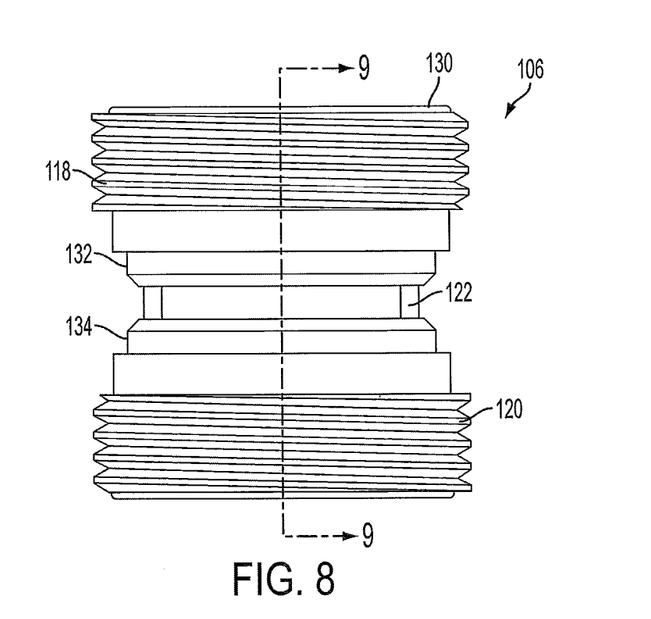
FIG. 8 is a front plan view of a shroud assembly of the laser profiler of FIG. 6.
Figure 9:
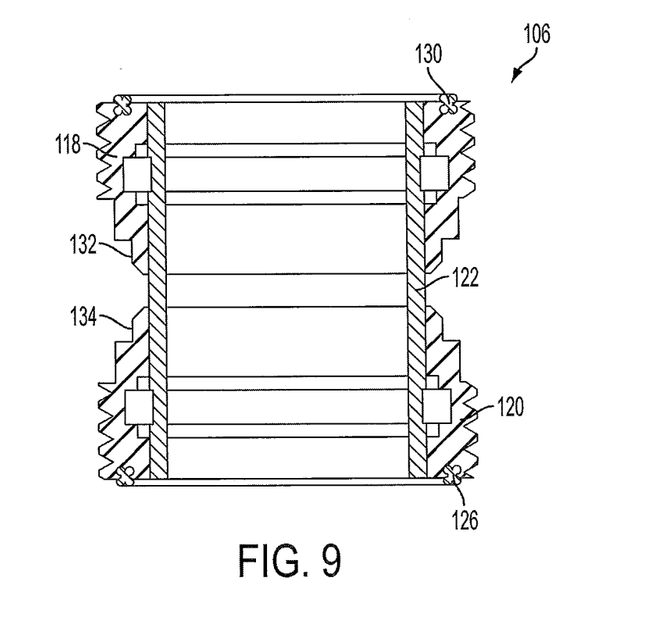
FIG. 9 is a cross-sectional view of the shroud assembly of FIG. 8 taken along line 9-9.

With specific reference to FIGS. 8 and 9, the shroud assembly 106 includes an upper threaded portion 118 and a lower threaded portion 120 with a transparent shroud 122 positioned therebetween. The conical mirror is positioned such that the light beam reflected therefrom exits the laser profiler 100 through the transparent shroud 122. The lower threaded portion 120 is threadedly connected to corresponding threads 124 of the base 104. A sealing device, such as a double o-ring seal 126, may be provided between the lower threaded portion 120 of the shroud assembly 106 and the base 104 to ensure that the cylindrical housing 102 is fluid tight. The upper threaded portion 118 is threadedly connected to corresponding threads 128 of the end cap 110. A sealing device, such as a double o-ring seal 130, may be provided between the upper threaded portion 118 of the shroud assembly 106 and the end cap 110 to ensure that the cylindrical housing 102 is fluid tight.

The upper threaded portion 118 includes an upper shielding portion 132 extending therefrom over a portion of the transparent shroud 122 and the lower threaded portion 120 includes a lower shielding portion 134 extending therefrom over a portion of the transparent shroud 122. The upper shielding portion 132 and the lower shielding portion 134 of the shroud assembly 106 are machined to a shape to shield misaligned light reflected from the conical mirror from passing through the transparent shroud 122 to ensure that the ring of light has a uniform width.

The laser profiler 100 of the alternative embodiment operates in a manner similar to the laser profiler 2 discussed hereinabove.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A laser profiler comprising:
a laser diode mounted within a substantially cylindrical housing;
a conical mirror positioned upstream from the laser diode within the cylindrical housing; and
a transparent shroud positioned to surround the conical mirror,
wherein, the cylindrical housing comprises a base, a shroud assembly having the transparent shroud positioned therein, and an end cap and the shroud assembly comprises an upper threaded portion threadedly coupled to the end cap, a lower threaded portion threadedly connected to the base, an upper shielding portion extending from the upper threaded portion and having a portion that tapers toward the transparent shroud such that the upper shielding portion extends over an upper portion of the transparent shroud, and a lower shielding portion extending from the lower threaded portion and having a portion that tapers toward the transparent shroud such that the lower shielding portion extends over a lower portion of the transparent shroud,
wherein a beam produced by the laser diode is directed to the conical mirror and is reflected therefrom at 360° through the transparent shroud to produce a ring of light, and
wherein the upper shielding portion is machined to have an outer diameter that is less than an outer diameter of the upper threaded portion and the lower shielding portion is machined to have an outer diameter that is less than an outer diameter of the lower threaded portion such that a shape of the upper shielding portion and the lower shielding portion shields misaligned light reflected from the conical mirror from passing through the transparent shroud to ensure that the ring of light has a uniform width.

2. The laser profiler of claim 1, wherein the transparent shroud is manufactured from borosilicate glass.

3. An apparatus for profiling an interior of a pipeline comprising:
a vehicle configured to be moved through the pipeline;
a laser profiler mounted on the vehicle and configured to project a 360° ring of laser light onto the interior of the pipeline, the laser profiler comprising:
a laser diode mounted within a substantially cylindrical housing;

a conical mirror positioned upstream from the laser diode within the cylindrical housing; and a transparent shroud positioned to surround the conical mirror, wherein, the cylindrical housing comprises a base, a shroud assembly having the transparent shroud positioned therein, and an end cap and the shroud assembly comprises an upper threaded portion threadedly coupled to the end cap, a lower threaded portion threadedly connected to the base, an upper shielding portion extending from the upper threaded portion and having a portion that tapers toward the transparent shroud such that the upper shielding portion extends over an upper portion of the transparent shroud, and a lower shielding portion extending from the lower threaded portion and having a portion that tapers toward the transparent shroud such that the lower shielding portion extends over a lower portion of the transparent shroud, wherein a beam produced by the laser diode is directed to the conical mirror and is reflected therefrom at 360° through the transparent shroud to produce the 360° ring of light, and wherein the upper shielding portion is machined to have an outer diameter that is less than an outer diameter of the upper threaded portion and the lower shielding portion is machined to have an outer diameter that is less than an outer diameter of the lower threaded portion such that a shape of the upper shielding portion and the lower shielding portion shields misaligned light reflected from the conical mirror from passing through the transparent shroud to ensure that the 360° ring of light has a uniform width; and a camera mounted on the vehicle configured to obtain an image of the 360° ring of light.

4. The apparatus of claim 3, wherein the vehicle is one of a self-propelled electric tractor and a sled pushed or pulled by a cable through the pipeline.

5. The apparatus of claim 3, wherein the transparent shroud is manufactured from borosilicate glass.

6. A method for profiling an interior of a pipeline, the method comprising:

providing a laser profiler, the laser profiler comprising:

a laser diode mounted within a substantially cylindrical housing;

a conical mirror positioned upstream from the laser diode within the cylindrical housing; and a transparent shroud positioned to surround the conical mirror, wherein, the cylindrical housing comprises a base, a shroud assembly having the transparent shroud positioned therein, and an end cap and the shroud assembly comprises an upper threaded portion threadedly coupled to the end cap, a lower threaded portion threadedly connected to the base, an upper shielding portion extending from the upper threaded portion and having a portion that tapers toward the transparent shroud such that the upper shielding portion extends over an upper portion of the transparent shroud, and a lower shielding portion extending from the lower threaded portion and having a portion that tapers toward the transparent shroud such that the lower shielding portion extends over a lower portion of the transparent shroud, wherein a beam produced by the laser diode is directed to the conical mirror and is reflected therefrom at 360° through the transparent shroud to produce a 360° ring of light, and wherein the upper shielding portion is machined to have an outer diameter that is less than an outer diameter of the upper threaded portion and the lower shielding portion is machined to have an outer diameter that is less than an outer diameter of the lower threaded portion such that a shape of the upper shielding portion and the lower shielding portion shields misaligned light reflected from the conical mirror from passing through the transparent shroud to ensure that the 360° ring of light has a uniform width;

projecting the 360° ring of light onto the interior of the pipeline;

moving the laser profiler through the pipeline;

imaging the 360° ring of light with a camera as it moves through the pipeline; and analyzing the images with software to produce a digital pipe profiler.

7. The method of claim 6, wherein the transparent shroud is manufactured from borosilicate glass.

* * * * *